(12) United States Patent
Merzenich et al.

(10) Patent No.: US 6,231,344 B1
(45) Date of Patent: May 15, 2001

(54) PROPHYLACTIC REDUCTION AND REMEDIATION OF SCHIZOPHRENIC IMPAIRMENTS THROUGH INTERACTIVE BEHAVIORAL TRAINING

(75) Inventors: Michael M. Merzenich; David T. Blake, both of San Francisco, CA (US)

(73) Assignees: Scientific Learning Corporation, Berkeley; The Regents of the University of California, Oakland, both of CA (US)

( * ) Notice: Subject to any disclaimer, the term of this patent is extended or adjusted under 35 U.S.C. 154(b) by 0 days.

(21) Appl. No.: 09/134,759

(22) Filed: Aug. 14, 1998

(51) Int. Cl.[7] .................................................. G09B 19/00
(52) U.S. Cl. .............................................................. 434/236
(58) Field of Search ................................... 434/236, 237, 434/238

(56) References Cited

U.S. PATENT DOCUMENTS

| | | | |
|---|---|---|---|
| 5,678,571 | 10/1997 | Brown | 128/898 |
| 5,722,418 | 3/1998 | Bro | 128/732 |
| 5,725,472 | 3/1998 | Weathers | 600/21 |
| 5,910,107 | 6/1999 | Iliff | 600/300 |
| 5,911,581 | * 6/1999 | Reynolds et al. | 434/236 |
| 5,913,310 | 6/1999 | Brown | 128/897 |
| 5,940,801 | * 8/1999 | Brown | 705/2 |
| 6,030,226 | * 2/2000 | Hersh | 434/236 |
| 6,053,739 | * 4/2000 | Stewart et al. | 434/236 |

FOREIGN PATENT DOCUMENTS

| | | | |
|---|---|---|---|
| WO 93/02622 | 2/1993 | (WO) | A61B/5/16 |
| WO 94/04072 | 3/1994 | (WO) | A61B/5/00 |
| WO 94/06088 | 3/1994 | (WO) | G06F/15/42 |
| WO 95/29447 | 11/1995 | (WO) | G06F/15/02 |
| WO 97/06730 | 2/1997 | (WO) | A61B/5/0484 |
| WO 97/34526 | 9/1997 | (WO) | A61B/5/05 |

OTHER PUBLICATIONS

Andrew J. Saykin, PsyD, et al., "Neuropsychological Function in Schizophrenia–Selective Impairment in Memory and Learning", Arch Gen Psychiatry, vol. 48, Jul. 1991, pp. 618–624.

Bruce E. Wexler, M.D., et al., "The Outpatient Treatment of Depression Implications of Outcome Research for Clinical Practice", The Journal of Nervous and Metal Disease, vol. 180, No. 5, May 1992, pp. 277–286.

Ralph H.B. Benedict, et al., "Effects of Attention Training on Information Processing in Schizophrenia", Schizophrenia Bulletin, vol. 20, No. 3, 1994, pp. 537–546.

Patrick W. Corrigan, et al., "Memory and vigilance training to improve social perception in schizophrenia", Schizophrenia Research, © 1995 Elsevier Science B.V., pp. 257–265.

Ian Creese, et al., "Dopamine Receptor Binding Predicts Clinical and Pharmacological Potentcies of Antischizophrenic Drugs", © 1976 American Assoc. for the Advancement of Science, Apr. 30, 1976, vol. 192, pp.481–483.

Ian Creese, et al., "Dopamine Receptors: A Classification", Dept. of Neurosciences, Journal of Clinical Psychopharmacology, © 1982 Williams & Wilkins, vol. 2, No. 5, pp. 329–335.

(List continued on next page.)

Primary Examiner—John Edmund Rovnak
(74) Attorney, Agent, or Firm—Beyer Weaver & Thomas, LLP (57) ABSTRACT

Computer-implemented perceptual and cognitive training techniques for remediating schizophrenia, either prophylactically prior to the onset of clinically observable schizophrenic behaviors or after the development of schizophrenia symptoms in a person. The computer-implemented behavioral exercises are designed to be sufficiently intensive, both in the number of repetitions and in the attentional focus related to task difficulty, such that permanent changes in neurotransmitter expression are achieved.

23 Claims, 5 Drawing Sheets

OTHER PUBLICATIONS

Ricardo Davila, PhD, et al., "Plasma Homovanillic Acid as a Predictor of Response to Neuroleptics", Arch Gen. Psychiatry, vol. 45, Jun. 1988, pp. 564–567.

Ann Delahunty, PhD., et al., "Rehabilitation of frontal/executive impairments in schizophrenia", Australian and New Zealand Journal Of Psychiatry, vol. 30, No. 6, Dec. 1996, pp. 760–767.

Colin D. Field et al., "Computer–Aided Cognitive Rehabilitation: Possible Application To The Attentional Defecit Of Schizophrenia, A Report Of Negative Results", © Perceptual and Motor Skills 1997, vol. 85, pp. 995–1002.

Michael F. Green Ph.D., "What Are the Functional Consequences of Neurocognitive Deficits in Schizophrenia?", Am J Psychiatry 153:3, Mar. 1996, pp. 321–330.

M. Hermanutz et al, "Computer–assisted Attention Training in Schizophrenics—A Comparative Study", © Springer–Verlag 1991, European Archives of Psychiatry and clinical Neuroscience 1991, pp. 282–287.

Amy R. Koreen, M.D., et al., "Plasma Homovanillic Acid Levels in First–Episode Schizophrenia—Psychopathology and Treatment Response", Arch Gen Psychiatry, vol. 51, Feb. 1994, pp. 132–138.

Heidi Nisbet et al., "Improving schizophrenic in–patients' Wisconsin card–sorting performance", © 1996 The British Psychological Society, British Journal Of Clinical Psychology (1996) vol. 35, pp. 631–633.

Toshiyuki Sawaguchi et al., "The Role of D1–Dopamine Receptor in Working Memory: Local Injections of Dopamine Antagonists Into the Prefrontal Cortex of Rhesus Monkeys Performing an Oculomotor Delayed–Response Task", Journal of Neuropsychiology, Feb. 1994, pp. 515–528.

Andrew J. Saykin, PsyD. et al., "Neuropsychological Deficits in Neuroleptic Naïve Patients with First–episode Schizophrenia", Arch Gen Psychiatry, vol. 51, Feb. 1994, pp. 124–131.

Wolfram Schultz et al., "A Neural Substrate of Prediction and Reward", Science, vol. 275, Mar. 14, 1997, www.sciencemag.org, pp. 1593–1599.

James Seltzer, Ph.D. et al., "Neuropsychological Rehabilitation in the Treatment of Schizophrenia", Connecticut Medicine, Sep. 1997, vol. 61, No. 9, pp. 597–608.

Theodore Van Putten, M.D. et al., "Plasma Homovanillic Acid as a Predictor of response to Fluphenazine Treatment", Psychopharmacology Bulletin, vol. 1, 1989, pp. 89–91.

Masataka Watanabe et al., "Increase of extracellular Dopamine in Primate Prefrontal Cortex During a Working Memory Task", © 1997 The American Psychological Society, pp. 2795–2797.

Bruce E. Wexler et al., "Normal neurocognitive performance after extended practice in patients with schizophrenia", © 1997 Elsevier Science B.V., pp. 173–180.

Graham V. Williams et al., "Modulation of memory fields by dopamine D1 receptors in prefrontal cortex", Nature, vol. 376, Aug. 17, 1995, pp. 572–575.

Daniel S. O'Leary, Ph.D et al., "Auditory Attentional Deficits in Patients with Schizophrenia—A Positron Emission Tomography Study", Arch Gen Psychiatry, vol. 53, Jul. 1996, pp. 633–641.

Dean F. Salisbury et al., "The N2 event–related potential reflects attention deficit in schizophrenia", Elsevier–Science B.V., Biological Psychology 39, 1994, pp. 1–13.

Karen Shedlack et al., "Language processing and memory in ill and well siblings from multiplex families affected with schizophrenia", © 1997 Elsevier Science B.V., vol. 25, pp. 43–52.

Stanley V. Catts, M.D. et al., "Brain Potential Evidence for an Auditory Sensory Memory Deficit in Schizophrenia", Am J Psychiatry 152:2; Feb. 1995, pp. 213–219.

U. Schall et al., "A left temporal lobe impairment of auditory information processing in schizophrenia: an event–related potential study", © 1997 Elsevier Science Ireland Ltd., Neuroscience Letters 229, pp. 25–28.

Michael F. Green Ph.D. et al., "Backward Masking Performance in Unaffected Siblings of Schizophrenic Patients—Evidence for a Vulnerability Indicator", Arch Gen Psychiatry, vol. 54, May 1997, pp. 465–472.

Kristin S. Cadenhead et al., "The Relationship of Information–Processing Deficits and Clinical Symptoms in Schizotypical Personality Disorder", © 1996 Society of Biological Psychiatry, vol. 40, pp. 853–858.

Sören Nielzén et al., "Perceptual Grouping due to Pitch and Amplitude in Hallucinating Schizophrenics", Psychopathology 1997, vol. 30, pp. 140–148.

Lynn E. DeLisi et al., "Schizophrenia as a chronic active brain process: a study of progressive brain structural change subsequent to the onset of schizophrenia", © 1997 Elsevier Science Ireland Ltd., Nuroimaging Section 74, pp. 129–140.

Sandra S. Kindermann et al., "Review of functional magnetic resonance imaging in schizophrenia", © 1997 Elsevier Science B.V., Schizophrenia Research 27, pp. 143–156.

Steven M. Silverstein et al., "Reduced Top–Down Influence in Auditory Perceptual Organization in Schizophrenia", Journal of Abnormal Psychology 1996,. vol. 105, No. 4, pp. 663–667.

Nagarajan et al., "Practice–Related Improvements in Somatosensory Interval Discrimination Are Temporally Specific But Generalize Across Skin Location, Hemisphere, and Modality," Feb. 15, 1998, The Journal of Neuroscience, pp. 1559–1570.

Merzenich et al., "Temporal Processing Deficits of Language–Learning Impaired Children Ameliorated by Training," Jan. 5, 1996, Science vol. 271, pp. 77–81.

Roger Jelliffe, et al., Adaptive control of drug dosage regimens: basic foundations, relevant issues, and clinical examples, International Journal of Bio–Medical Computing 36 (pp. 1–23), © 1994.

Schneider et al. Self–Regulation of Slow Cortical Potentials in Psychiatric Patients: Schizophrenia, © Dec. 1992, Biofeedback and Self–Regulation, vol. 17, No. 4, pp. 277–292.

Tretter, F., Perspectives of Computer–Aided Therapy and Rehabilitation in Psychiatry, Jul. 1996, pp. 475–486.

Hermanutz M. and Gestrich, J., Computer–assisted Attention Training in Schizophrenics, 1991, European Archives of Psychiatry and Clinical Neuroscience, vol. 240, pp. 282–287.

Frith, C., The role of the prefrontal cortex in self–consciousness: the case of auditory hallucinations, pp. 1505–1512 (1996).

* cited by examiner

PROPHYLACTIC REDUCTION AND REMEDIATION OF SCHIZOPHRENIC IMPAIRMENTS THROUGH INTERACTIVE BEHAVIORAL TRAINING

BACKGROUND OF THE INVENTION

The present invention relates to interactive behavioral training techniques for remediating schizophrenia. More specifically, the present invention relates to perceptual and cognitive training techniques for remediating schizophrenia, either prophylactically prior to the onset of clinically observable schizophrenic behaviors or after the development of schizophrenia symptoms in a person.

Evidence suggests that about 1 in 100 individuals is schizophrenic and about 1 in 25 individuals is "at-risk" for schizophrenia onset. Schizophrenia is generally regarded as one of the most devastating of the common forms of mental illness. It generally arises in young adults between about 16 and 30 years of age. Most individuals that develop the illness have behavioral characteristics that identify them as "at risk" for schizophrenia onset from early childhood.

Risk is contributed to by inherited factors. At the same time, there is a long history of studies that indicates that onset of the "illness" is modulated by the behavioral experiences of at-risk individuals. Even in the case of identical twins, less than half of their genetically identical siblings develop the illness. At the same time, given underlying genetic factors contributing to the risk of onset of the illness, the historical occurrence of schizophrenia in a family is one simple way of defining "at risk" status for young adults.

The illness generally arises progressively through a period of increasingly abnormal behaviors that may be identified over a prodromal epoch that is several weeks to many months in duration. Commonly beginning with a feeling that "things just don't seem (look, feel, sound) right," it ultimately progresses to the emergence of uncontrolled delusions and hallucinations that are a hallmark of the full-blown illness.

Because the causes of schizophrenia are not fully understood, contemporary schizophrenia treatment typically consists of antipsychotic medications (i.e., neuroleptics) that are chosen on the basis of their ability to reduce schizophrenic symptoms and/or lessen the chances that symptoms will return. By way of example, conventional neuroleptics such as haloperidol, chlorpromazine, or thioridazine have long been employed for controlling acute schizophrenic symptoms and for improving the functioning of people with schizophrenia, thereby reducing the need for hospitalization.

Although the use of antipsychotic medications have proven effective for controlling certain schizophrenic symptoms (e.g., hallucinations, paranoia, delusions), there are disadvantages to the pharmacological-based approach. By way of example, it is known that certain antipsychotic medications are not effective, for reasons unknown, on some subjects. Even when a medication is found to be effective for a particular patient, the prolonged use of an antipsychotic medication may give rise to unwanted side effects, such as dependency, drowsiness, restlessness, muscle spasms, tremor, dry mouth, and/or blurring of vision. Still further, it is believed that one of the long term side effects of antipsychotic drugs is the development of tarditive dyskinesia (TD). TD is a disorder typically characterized by involuntary movements most often affecting the mouth, lips, and tongue and sometimes the trunk or other parts of the body. Still further, antipsychotic drugs do not effectively ameliorate negative symptoms of schizophrenia in most patients, e.g., they do not restore normal speech reception abilities, long term memory abilities, or many other related cognitive deficits that limit a patient's potential and achievement.

In view of the foregoing, there are desired therapeutic techniques that can remediate schizophrenia or prevent its onset without introducing unwanted side effects. In particular, there are desired schizophrenia treatments, prophylactic or otherwise, that do not require or that reduce the need for antipsychotic medication.

SUMMARY OF THE INVENTION

The present invention relates, in one aspect, to perceptual and cognitive training techniques for remediating schizophrenia, either prophylactically prior to the onset of clinically observable schizophrenic behaviors or after the development of schizophrenia symptoms in a person.

In one embodiment, schizophrenia is prevented or remediated by engaging the subject in computer-implemented interactive behavioral training exercises designed to maximize changes in the release of cortical neurotransmitters (such as dopamine, acetylcholine, or the like) in the forebrain, thereby ameliorating expressions of schizophrenia that are believed to be attributable to this imbalance. Preferably, the computer-implemented behavioral exercises are designed to be sufficiently intensive, both in the number of repetitions and in the attentional focus related to task difficulty, such that permanent changes in neurotransmitter expression are achieved. Since the invention seeks to create permanent changes in neurotransmitter expression in the forebrain, the number of repetitions and the attentional focus required are typically far in excess of what is required to simply improve an isolated skill.

In accordance with one embodiment, the computer-implemented behavioral exercises are also implemented such that the subject is rewarded in a majority of the trials to encourage and magnify neurochemical release and to continue to motivate the subject to maintain sharply focused attention and vigilance, thereby ensuring permanent changes in neurotransmitter expression in the subject.

In one embodiment, the computer-implemented exercises are designed to also simultaneously improve the subject's perceptual, cognitive, social and executive function skills while at the same time addressing the neurochemical imbalance that underlies the schizophrenia symptoms. Preferably, the computer-implemented exercises employ cross-stimulus sets to promote inter-related and synergistic combinations of perceptual, cognitive, social, and executive skills.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which like reference numbers refer to like items and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

A. Theories

Studies of schizophrenia origin and expression have demonstrated that experiential factors contribute substantially to its genesis. There is also evidence that suggests that that the "break" manifested by the first unmistakable clinical signs of schizophrenia is preceded by a long, experientially-modulated progression of behavioral and (probably consequent) physical changes in the brain of an at-risk (or schizophrenic) individual. Before and after the onset of the first-episode of schizophrenic "break", schizophrenics have been demonstrated in many studies to have degraded abilities at tasks requiring short-term verbal working memory, rapidly associated cognitive "prediction" or "expectation", or ongoing attention/vigilance control. Schizophrenics who have auditory hallucinations (which describe the majority of afflicted individuals) also have a strongly correlated degradation in their speech reception abilities. Schizophrenics also have social and executive function skills deficits, e.g., deficits and confusions in identifying the moods or reactions of others, in determining what for them is a socially correct course of action, in identifying the sources of current and past actions or events, etc.

We hypothesize that the "break" resulting in a diagnosis of schizophrenia arises from a disruption of the ability of the cortex to maintain reliable associations between a) memory/prediction/expectation-based representations and b) immediate, ongoing neurological representations of inputs and actions. A large body of facts in scientific evidence appears to be consistent with this hypothesis. Activities in brain areas that are critically involved in these associations tend to be lower in schizophrenics than in normals. In some studies, up to two thirds of schizophrenics do not show normal evoked neurological responses to novel or surprising stimuli. The other third may be unable to habituate (decrease) their responses to what are initially novel stimuli, even while they are presented repetitively on a boring schedule in which they would be strongly habituated in any normal individual. All of these deficits are consistent with the hypothesis that schizophrenics fail to identify inputs as "expected" or "predicted" or "unexpected" or "unpredicted": their capacities for ongoing prediction on the basis of immediate or past "stored information" or "knowledge" are believed to be defective.

In functional imaging studies in schizophrenics, cortical areas tend to have weaker responses when they are engaged in tasks that require ongoing expectation or prediction, or other aspects of short term memory or task "vigilance" than are recorded in normal subjects. Evoked brain responses associated with short-term and long-term memory-based predictions (expectations) about events in an event stream or that signal an event as "expected" and "predicted" or "novel" and "surprising" tend to be grossly abnormal in schizophrenics, consistent with an emergent breakdown in this critical associative system.

The neurologically evoked responses related to the representations of unexpected events in entry-level cortical areas (e.g., the primary auditory cortex or A-1) manifested by specific brain potential responses tend to be weaker in schizophrenics than in normals. The degradation of speech reception abilities recorded in schizophrenics who have auditory hallucinations is a predicted consequence of a breakdown of the reciprocal connections between cortical areas representing incoming speech inputs and ongoing predictions and expectancies that contribute powerfully to speech reception through the operation of this critical associative system. In such a disconnected system, a degradation in "vigilance" and "attentional" control is expected. And in such a disconnected system, the association/memory-based identification of the complex cues signaling appropriate social responses, or identifying the sources of action are also be expected to be impaired.

It might be noted that the complex systems of associative connections by which the brain relates things learned, remembered, predicted and expected to its moment-by-moment representations of input and action events is established, in an ideosyncratic form in every human brain, by brain plasticity-based learning. Stability in the continuous associations between things remembered over the long or short term and things happening in the present moment is established and maintained across childhood and young adulthood by progressive, learning-based brain plasticity. While the mechanisms underlying the massive brain plasticity that underlie the establishment of these very complex associative relationships are common to all brains, the actual repertoires of things learned and remembered to be associated moment by moment with ongoing activities—and the strength, reliability and stability of those associations—are different in every human individual.

It is probable that complex genetic factors that can increase the risk of schizophrenia onset in at-risk individuals contribute to a weakness in this associative learning that results in a development of progressively less reliable and less stable associating brain connections that relate memories and the immediate past to the representations of the present. At the same time, it is noteworthy that in even genetically identical (monozygotic) twins in which one twin develops schizophrenia, nearly 60% of their genetically identical siblings never develop the "illness". The literature indicates that differences in ideosyncratic experiential histories are one important source of their "protection".

It should also be noted that the weaknesses that ultimately result in a schizophrenic "break" are often signaled as "risk factors" evident many years prior to "disease" onset, commonly expressed in observable behavioral differences in language, movement, social skills, et al., apparent in at-risk children and young adults.

It is believed that learning/memory-induced changes in the cerebral cortex are modulated by powerful neurotransmitters, which are released in the forebrain under specific behavioral conditions on each successive and appropriately "rewarded" learning trial. Dopamine and acetylcholine are believed to be two of the most important of a number of neurotransmitters that have powerful modulatory effects, gating physical brain changes in learning, signaling that the cortex "record" the learned or remembered event or behavior in the normal human brain, and evoking sensations and controlling moods associated with "reward" (e.g., "pleasure"). Over the course of a day, the cerebral cortex is bombarded by very many thousands of sensory input events, generates countless brain-based activities, and controls thousands of neuronally initiated and controlled actions. The modulatory control systems in the brain essentially signal the brain plasticity mechanisms to "record" input events, activities or actions, with the "record button" being "pushed" as a function of the brain's evaluation of the behavioral significance of those events, activities or actions. For example, evidence suggests that neither dopamine nor acetylcholine is released when inputs received by the brain occur while a subject is sleeping, is not paying attention to them, is not aware of inputs, activities or actions, or is performing an action "automatically" without conscious awareness of its specific details.

On the other hand, evidence suggests that both are released trial by trial in the learning phase or in the learning-based elaboration of a new or progressively elaborated perceptual, cognitive or social or executive-function behavioral skill or ability. The release of both transmitters is dramatically attenuated once that skill is mastered. The release of one or both neurotransmitters is also powerfully modulated as a function of the intensity with which a skill is learned, commonly paralleling the intensity of attentive focus related to task difficulty. The release of both is also proportionally greater when the behavioral "reward" is greater.

It is believed, therefore, that both dopamine and acetylcholine modulation strongly contribute, through their gating of brain plasticity changes, to the development of controlled associative connections related to short term memory/ expectation/prediction/vigilance operations, and to the maintenance of reliable, high-fidelity representations of speech, language, visual, motor and other neural "representations" at the perceptual, cognitive and executive-function level. Dopamine is specifically implicated in short term memory/expectation/prediction/vigilance operations, but it is also an important modulator of learning-induced plasticity in general, especially in the sensory-motor and auditory/ speech skill acquisition domains. Acetylcholine is a powerful modulator of progressive (procedural and cognitive) skill learning and of non-declarative memory. The dopamine-releasing and acetylcholine-releasing control systems are also directly interactive; dopamine-containing neurons engage inputs that can positively induce cortically-projecting acetylcholine-containing neurons in the basal forebrain.

In animal model systems including studies conducted in our laboratory, both dopamine and acetylcholine have been shown to induce powerful brain plasticity changes in non-behaving animals, one of a number of lines of evidence that suggests that they directly engage the "control button" governing learning-based cortical plasticity, i.e., governing local neural network connectional "rewiring" to create enduring (remembered) stimulus-specific, plan-specific and action-specific representational constructs.

Further, both dopamine and acetylcholine expressions appear to be grossly abnormal in the cerebral cortex and subcortex in schizophrenics. As mentioned, the principal classical method to treat schizophrenia is to apply a "neuroleptic" drug, which may block a specific dopamine and/or other receptors, thereby attenuating the effects of dopamine mediated by that receptor (primarily located subcortically), hypothetically reducing its specific action(s). The predominant neuroleptics applied most frequently in the current era have more complex neuropharmacological effects on the actions and expressions of dopamine, serotonin, acetylcholine, noradrenaline, and other transmitters.

It is believed that a progressive degradation in the control of memory/expectation/prediction/vigilance re real-time activity results in a progressive and ultimately massive alteration in the schedule of behaviorally "rewardable" cortical activity. Relatively few events and actions represented by ongoing activities in the cortex are judged, by brain mechanisms, to be "correct" or "successful" or "expected" or "predicted". Almost thousands of events each day are interpreted as "incorrect" or "unsuccessful" or "unexpected" or "unpredicted". That results in a substantial cerebral cortex-wide change of dopamine and acetylcholine expression and activation, which further exacerbates an associative disconnection problem that requires learning-induced change to maintain or repair itself.

We hypothesize that abnormal cortical dopamine levels signal subcortical dopamine sources to upregulate dopamine production as a part of the natural response to this "disconnection". Studies of dopamine levels recorded in schizophrenics indicate that there are at least two positive actions of the dopamine receptor blocker-acting neuroleptic drug that are consistent with this view. First, blocking the D2 receptor for dopamine (the action of most "neuroleptics" administered to schizophrenics) significantly reduces the subcortical consequences of very high dopamine levels. Second, blocking the D2 receptor results in an increase in cortical dopamine levels in trial-by-trial learning in the cortex, and in an amplification of the memory/learning-directed modulatory actions of dopamine in the cerebral cortex.

We have tested the hypothesis that higher subcortical dopamine release is a response to altered cortical signals and to consequent altered cortical dopamine release by determining the impacts of engaging a patient in talking about their psychotic illusions. In control studies, patients talk about other, non-illusory subjects on a similar schedule. In the former case, signature affects associated with subcortical dopamine release go up: the subject becomes substantially more intense, more violent, more emotional. In parallel, their cortically-based auditory hallucinations are significantly suppressed, consistent with a modestly elevated expression of cortical dopamine.

Note that by this hypothetical scenario of schizophrenia origin, this imbalance in dopamine (and acetylcholine) effects in the subcortex and cortex is caused by a progressive weakening and ultimately a break in the learning/brain plasticity-based control of associations between memories, expectancies, predictions and vigilance with ongoing events and actions. With that "break" in place, dopamine and acetylcholine expressions are rapidly and radically altered in the cerebral cortex. The subcortical sources of dopamine respond to that altered expression and by changing cortical signaling by increasing their dopamine production, stores and activities. From these observations, it is believed that all of these progressive changes can be prevented from happening—or can be reversed—by appropriate intensive dopamine and acetylcholine system-engaging perceptual, cognitive and social and executive-function skills training.

Also note that these abnormal transmitter levels do not forestall the successful engagement of the cortex in learning at precisely the kind of perceptual and cognitive and social and executive skills that are defective in schizophrenics. Limited, piecemeal studies of subjects trained in all of these sensory/perceptual/cognitive skills areas have already shown that they can achieve normal or supernormal abilities through progressive training in individual tasks that they are engaged in, in each of the skill domains targeted.

B. General Philosophy of the Inventive Technique

From the foregoing, it is believed that schizophrenia may be diagnosed by a battery of interactive perceptual and cognitive tests to define the at-risk status of a human subject, typically a young adult, to define their "safety margin" for schizophrenia onset, and to optionally define their "safety margin" for a relapse.

Further, it is believed that the risks of schizophrenia may be prevented or remediated by engaging the subject in interactive behavioral training exercises designed to maximize changes in the cortical dopamine and acetylcholine (and other neurotransmitters) release to restore a more normal neurotransmitter balance in the forebrain, thereby ameliorating expressions of schizophrenia (e.g., delusions, hostilities, etc.) that are believed to be attributable to this imbalance. In so doing, the interactive behavioral exercises are designed to be sufficiently intensive, both in repetition and in the attentional focus related to task difficulty, such that permanent changes in neurotransmitter expression are achieved.

Further, the interactive behavioral exercises are designed so that the subject is rewarded (i.e., for being correct) in a majority of the trials. Preferably, the exercises are configured such that the subjects can respond correctly and be rewarded at least 50% and more preferably at least about 80% of the trials attempted. In other words, the interactive behavioral exercises are configured to exercise the "record button" with such intensity such that the neurotransmitter modulatory apparatus functions become at least partially restored in schizophrenics. In contrast with prior art techniques, which tend to approach each isolated skill on a piecemeal basis in order to improve the patient's performance with regard to the specific skill being focused upon, the invention requires driving the subject at such intensity (in terms of the number of trials and attentional focus per day and far in excess of what is required to simply achieve improvement in an isolated skill) that the underlying mechanisms that modulate neurotransmitter expressions are fundamentally changed.

In general, the training exercises may be selected for their abilities to engage the patients intense, trial-by-trial attentional focus while at the same time ensuring that the patients are substantially rewarded for correct performances a substantial percent of the time. Accordingly, the stimuli and required responses associated with the training exercises may vary widely, and may not necessarily directly correspond to the skill identified as deficient in the patient. In so doing, it is not necessary that the training or responses be complex or geared specifically to any complex skill that is identified as deficient. Of course, as will be discussed later herein, training efficiency may be increased by designing training exercises to also simultaneously improve one or more the subject's perceptual, cognitive, and executive function skills that are identified as impaired.

Thus, it is now possible to simplify training exercises to the point where the constant minute-by-minute monitoring, engagement of, or interaction with a health care professional is not required. Specifically, the training exercises may be geared toward interactive types of exercises that may be administered using today's computing apparatus. This again is different from the prior art approach such as psychotherapy or vocational/social counseling, wherein the complex nature of the interaction with the patient typically necessitates the presence of the health care provider.

As mentioned before, the training exercises may be designed to also simultaneously improve the subjects perceptual, cognitive, and executive function skills while at the same time addressing the neurochemical imbalance that underlies the schizophrenic symptoms. Preferably, the training exercises are designed to be extensive with regard to each of these skills, with hundreds of trials for each skill trained per day. Even more preferably (but not absolutely necessary), the exercises may employ cross-stimulus sets that would promote an inter-related and synergistic combination of perceptual, cognitive, social skills, and executive skills function capabilities. To maintain the aforementioned intensity, the stimulus sets and task challenges are preferably adjustable over time to keep up with the subject's improvements. In this respect, the invention differs from the prior art in that the training herein is intended to drive the underlying neurochemical changes and although the exercises may be selected for their efficacy in improving a specifically identified defective skill, the intensity (in the number of repetitions per training day and the attentional focus) and emphasis on rewards are far beyond what is normally required in the prior art to simply improve a specific skill.

C. Exemplary Implementations

Figure 1A:
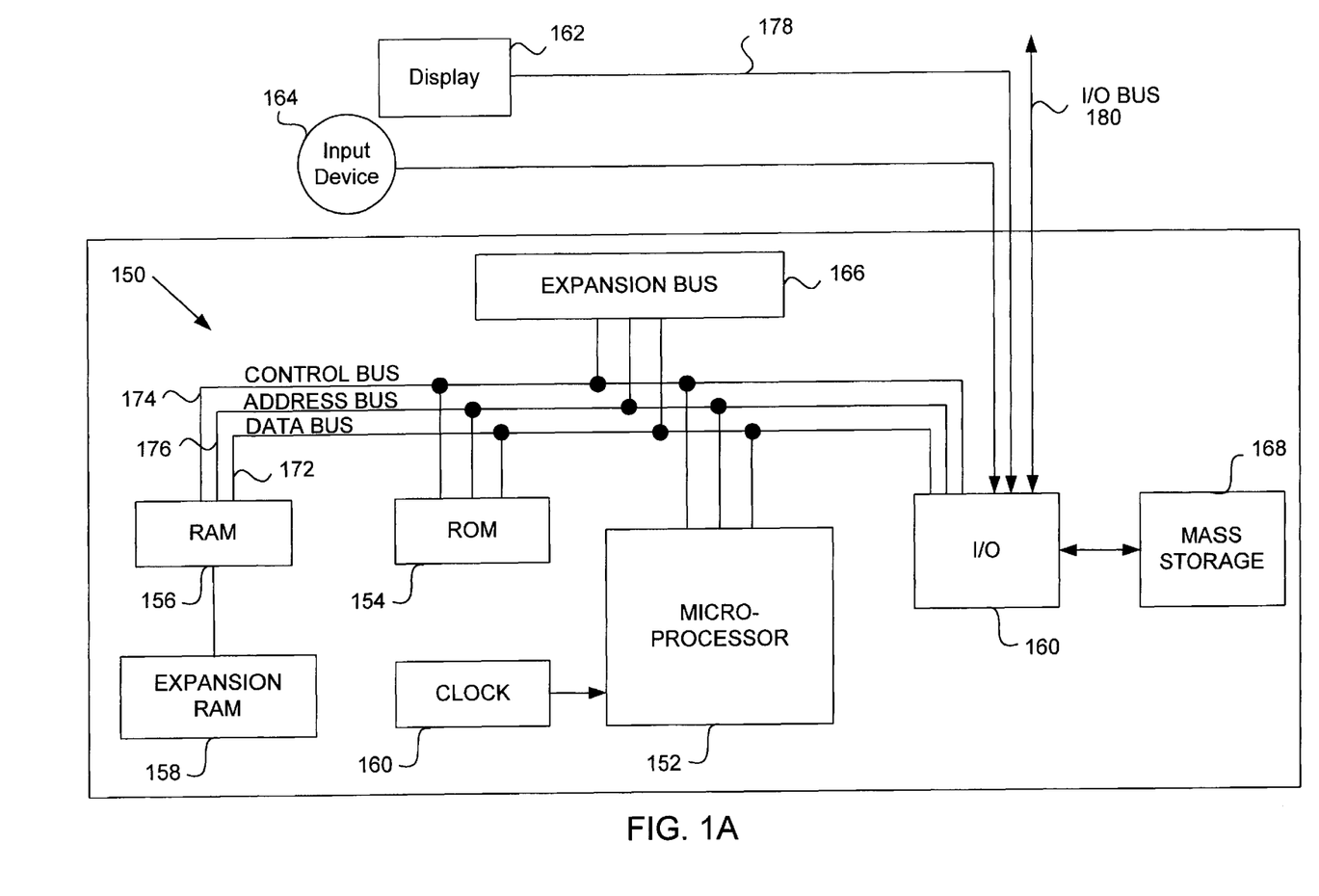
FIGS. 1A and 1B illustrate, in accordance with one embodiment of the invention, the computer-controlled apparatus for administering interactive behavioral exercises that assess schizophrenia risks and/or prevent or remediate schizophrenic impairments.
Figure 1B:
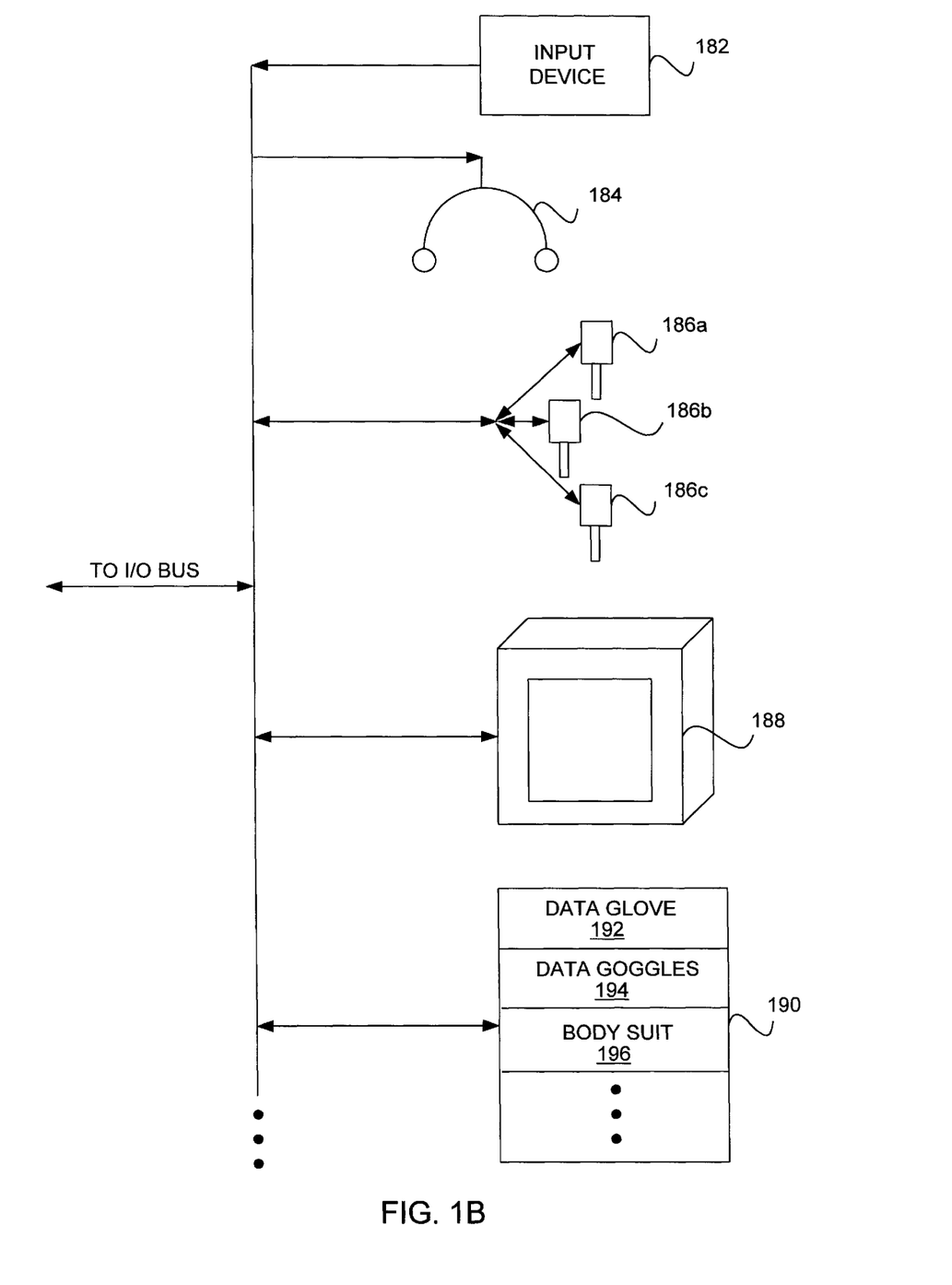

The features and advantages of these aspects of the invention, as well as other aspects of the present invention, may be better understood with reference to the figures and discussions that follow. As mentioned earlier, the schizophrenia assessment and prevention/remediation exercises of the present invention are preferably implemented using computer-based apparatus. FIGS. 1A and 1B illustrate, in accordance with one embodiment of the invention, an exemplary computer-controlled apparatus, including computer 150, for delivering computer-controlled stimuli to assess a subject for schizophrenia risks as well as to train a subject to remediate schizophrenia or prevent the onset of clinically observable schizophrenic symptoms. As the terms are employed herein, assessment refers generally to ascertaining a test subject's risk for developing clinically observable schizophrenic symptoms or the subject's degree of affliction if there has already been the onset of schizophrenia. Training on the other hand may be applied to subjects whose risk factors are sufficiently high to warrant prophylactic measures as well as subjects who have already exhibited clinically observable schizophrenic symptoms.

Referring to FIG. 1A, a computer system 150 in accordance with the present invention includes a central processing unit (CPU) 152, read only memory (ROM) 154, random access memory (RAM) 156, expansion RAM 158, input/output (I/O) circuitry 160, display assembly 162, input device 164, and expansion bus 166. Computer system 150 may also optionally include a mass storage unit 168 such as a disk drive unit or nonvolatile memory such as flash memory and a real-time clock 160. In one embodiment, mass storage unit 168 may include units which utilize removable computer readable media, such as floppy disks, opto-magnetic media, optical media, and the like for the storage of programs and data.

CPU 152 is preferably a commercially available, single chip microprocessor such as one of the Intel X86 (including Pentium™ or PentiumII™) or Motorola 680XX family of chips, a reduced instruction set computer (RISC) chip such as the PowerPC™ microprocessor available from Motorola, Inc., or any other suitable processor. CPU 152 is coupled to ROM 154 by a data bus 172, control bus 174, and address bus 176. ROM 154 may partially contain the basic operating system for the computer system 150. CPU 152 is also connected to RAM 156 by busses 172, 174, and 176 to permit the use of RAM 156 as scratch pad memory. Expansion RAM 158 is optionally coupled to RAM 156 for use by CPU 152. CPU 152 is also coupled to the I/O circuitry 160 by data bus 172, control bus 174, and address bus 176 to permit data transfers with peripheral devices.

I/O circuitry 160 typically includes a number of latches, registers and direct memory access (DMA) controllers. The purpose of I/O circuitry 160 is to provide an interface between CPU 152 and such peripheral devices as display assembly 162, input device 164, mass storage 168, and/or any other I/O devices. I/O circuitry 160 may also include analog-to-digital (A/D) converters, digital-to-analog (D/A) converters, as well as other control circuits for controlling and receiving feedback data from the I/O devices. The I/O devices suitable for generating stimuli to be administered to the test subject and for receiving responses therefrom may be coupled to I/O bus 180 of computer 150. They are discussed in greater detail with reference to FIG. 1B. Display assembly 162 of computer system 150 is an output device for displaying objects and other visual representations of data, as well as for generating visual stimuli in one embodiment The screen for display assembly 162 can be a device that uses a cathode-ray tube (CRT), liquid crystal display (LCD), or the like, of the types commercially available from a variety of manufacturers. Input device 164 can be a keyboard, a mouse, a stylus working in cooperation with a position-sensing display, or the like. Alternatively, input device 164 can be an embedded RF digitizer activated by an "active" RF stylus. As a further alternative, input device 164 may be any type of switch capable of communicating a test subject's response to computer system 150. Therefore, as used herein, the term input device will refer to any mechanism or device for entering data and/or pointing to a particular location on a screen of a computer display. One or more input devices may be provided to control computer 150 and/or to receive responses from the test subject. The aforementioned input devices are available from a variety of vendors and are well known in the art.

Some type of mass storage 168 is generally considered desirable. However, mass storage 168 can be eliminated by providing a sufficient amount of RAM 156 and expansion RAM 158 to store user application programs and data. In that case, RAMs 156 and 158 can optionally be provided with a backup battery to prevent the loss of data even when computer system 150 is turned off. However, it is generally desirable to have some type of long term mass storage 168 such as a commercially available hard disk drive, nonvolatile memory such as flash memory, battery backed RAM, PC-data cards, or the like.

In FIG. 1B, some exemplary stimuli generators are shown, including headphone 184 (for delivering auditory stimuli), computer-controlled probe 186 (for delivering touch stimuli), visual stimuli generator 188 (for delivering visual stimuli), and/or virtual reality apparatus 190 (for delivering stimuli to and receiving responses from the test subject in a virtual manner through any of the senses). In general, these I/O devices may interface with computer system 150 via I/O circuit 160 or an appropriate interface circuit, which may be external to computer 150 and/or dedicated to the I/O device. Visual stimuli generator 188 may represent, for example, any light generating device such as a light bulb, a flash device, another computer display screen or the like if such is employed instead of display screen 162 of computer 150 for providing visual stimuli to the test subject. Virtual reality apparatus 190 may include, for example data glove 192, virtual goggles 194, body suit 196, or the like, each of which may be able to both deliver the stimuli to the test subject as well as sense the responses therefrom. An optional input device 182 is also shown, representing a dedicated input device, such as a switch, for receiving responses from the test subject. Optional input device 182 is provided when it is desired to receive responses to the test stimuli from the test subject through an input device other than input device 164 of computer 150. Other optional devices (not shown) may also be provided and contain therein transducer to receive other types of responses from the subject. By way of example, a microphone may be provided to receive verbal responses from the client to be processed by the computer.

In operation, computer system 150 is employed to generate control signals to the stimuli generator(s) to produce the stimuli of the various tests. These stimuli are then furnished to the test subject for assessment and/or training, and the responses from the test subject may then be recorded by input device 164 and/or input device 182 (or another suitable input device) and analyzed by CPU 152. If desired, feedback (both positive and negative with emphasis preferably on the positive) to the test subject may be given at various stages of the test(s) via, for example, display assembly 162.

It should be borne in mind that although computer system 150 is discussed in some detail herein to facilitate discussion, the invention itself may be practiced using a variety of suitable computer-implemented techniques. In general, any suitable computer system may be employed for generating control signals to the stimuli generators and receive feedback from the input device(s). Further, the inventive training technique disclosed herein may be implemented via a computer network, such as a local area network (LAN), wide area network (WAN) or a global computer network such as the Internet (also popularly known as "the Web"). In the latter cases, the inventive computer-implemented assessment and/or training technique may be implemented at least in part as downloadable computer software and/or data (e.g., applets such as JAVA™ applets from Sun Microsystems Inc.). The downloadable computer software and data may be kept on one or more servers on the network, accessible by any client computer or terminal capable and authorized for such access (via, for example, a web browser). The client computer/terminal may then be employed to control an appropriate stimuli generator and to gather responses from the test subject. To facilitate testing, the downloadable computer software and data can be downloaded once and reused over and over at the client computer/terminal. Alternatively, the downloadable computer software and data can be downloaded for each individual testing session via the network as needed. In some cases, the computer software may be executed at the servers themselves, with program outputs transmitted to the client computer/terminal for interfacing with the I/O devices. Alternatively, execution may take place locally at the client computer/terminal after downloading. Data pertaining to the client's responses may be transmitted to another computer on the network to permit a remote health care professional to monitor the patient's participation and progress simultaneously or on a periodic basis. Network computing techniques and implementations therefor are well known in the art and are not discussed in great detail here for brevity's sake.

As mentioned earlier, interactive behavioral exercises may be employed to assess an individual's risk for developing schizophrenia even prior to the onset of clinically observable schizophrenic symptoms. The interactive behavioral exercises may be tailored to assess one's abilities at tasks requiring, for example, short-term working memory, rapidly associated cognitive prediction (or expectation), or ongoing vigilance/attention control.

Figure 2:
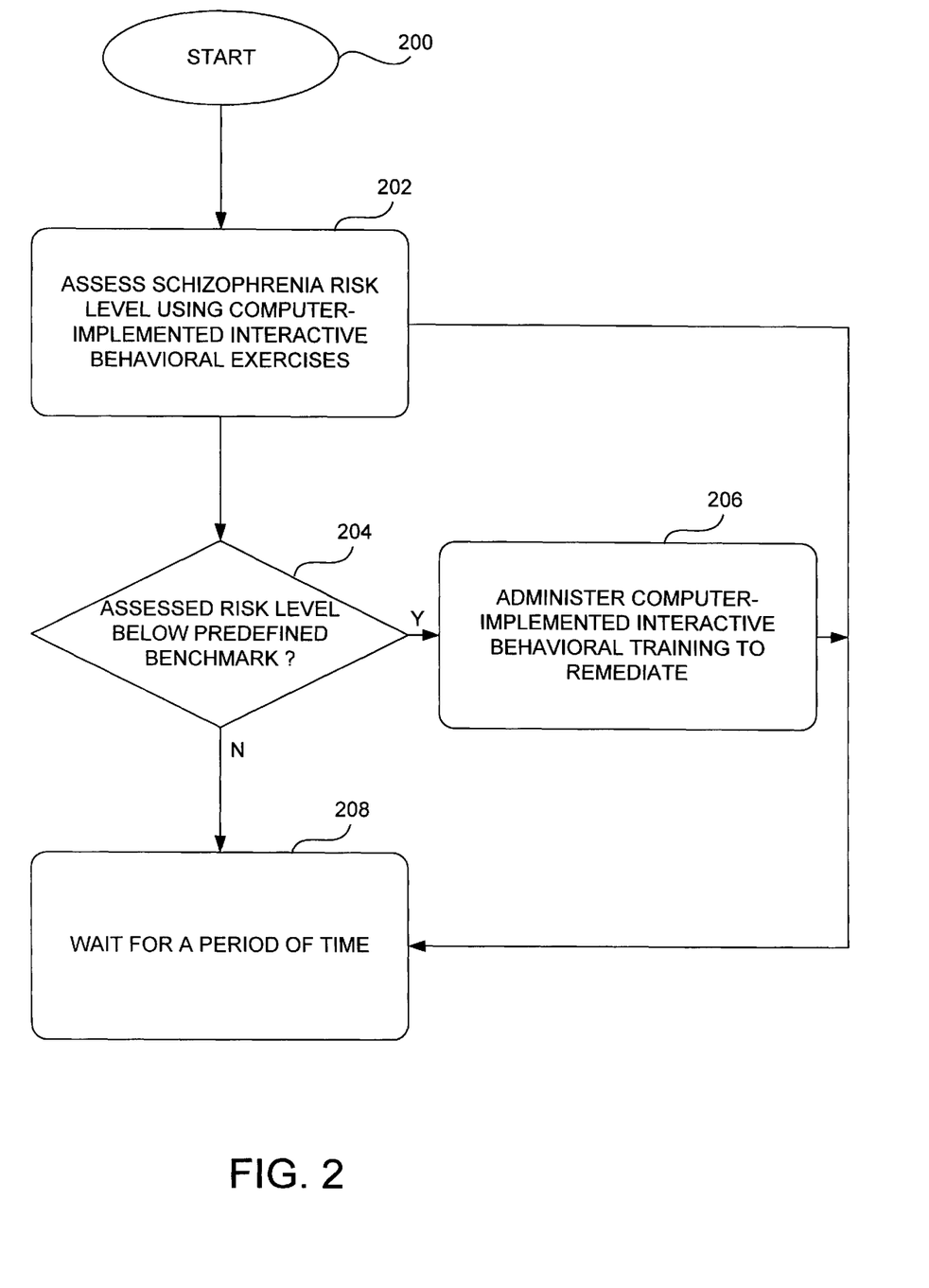
FIG. 2 illustrates, in accordance with one aspect of the present invention, the inventive method of employing interactive behavioral exercises to assess one's risk level on an ongoing basis and if appropriate, employ interactive behavioral training to remediate or as a prophylactic.

FIG. 2 illustrates, in accordance with one aspect of the present invention, the inventive method for employing interactive behavioral exercises to assess one's risk level on an ongoing basis and if appropriate, employ interactive behavioral training to remediate or as a prophylactic. In step 202, the interactive behavioral exercises are administered to a subject using computer-implemented behavioral interactive exercises. In the typical scenario, the interactive behavioral exercises are administered to those deemed statistically at-risk (e.g., relatives of schizophrenics) or to anyone suspected of being at-risk for developing schizophrenia later on. The subject's performance on the computer-implemented interactive behavioral exercises is then compared against a predefined benchmark (204). The predefined benchmark may be, for example, the performance expected of a normal or the minimal performance below which degraded abilities are indicated. The exact benchmark of course depends on the nature of the exercises administered.

If the subject's performance is below the predefined benchmark, interactive behavioral training is administered, using computer-implemented interactive behavioral training exercises, to remediate (step 206). One may think of the interactive behavioral exercises as being given prophylactically since the subject may not have exhibited clinically observable schizophrenic symptoms such as delusions or hallucinations. Of course, the subject's poor performance on the interactive behavioral exercises given during assessment may indicate some abilities have already been degraded.

After training, the subject may be tested again in step 202 to ensure that sufficient progress has been made. Additional training may be required (loop 202/204/206) until the subject's performance increases.

Alternatively, if the performance is above the predefined benchmark, the subject may be retested after a period of time (step 208) to permit the subject to be monitored for schizophrenia risk over time. In this manner, the assessment steps of FIG. 2 employ the performance results of the interactive behavioral exercises to define and maintain a safe operational position on an on-going basis.

Figure 3:
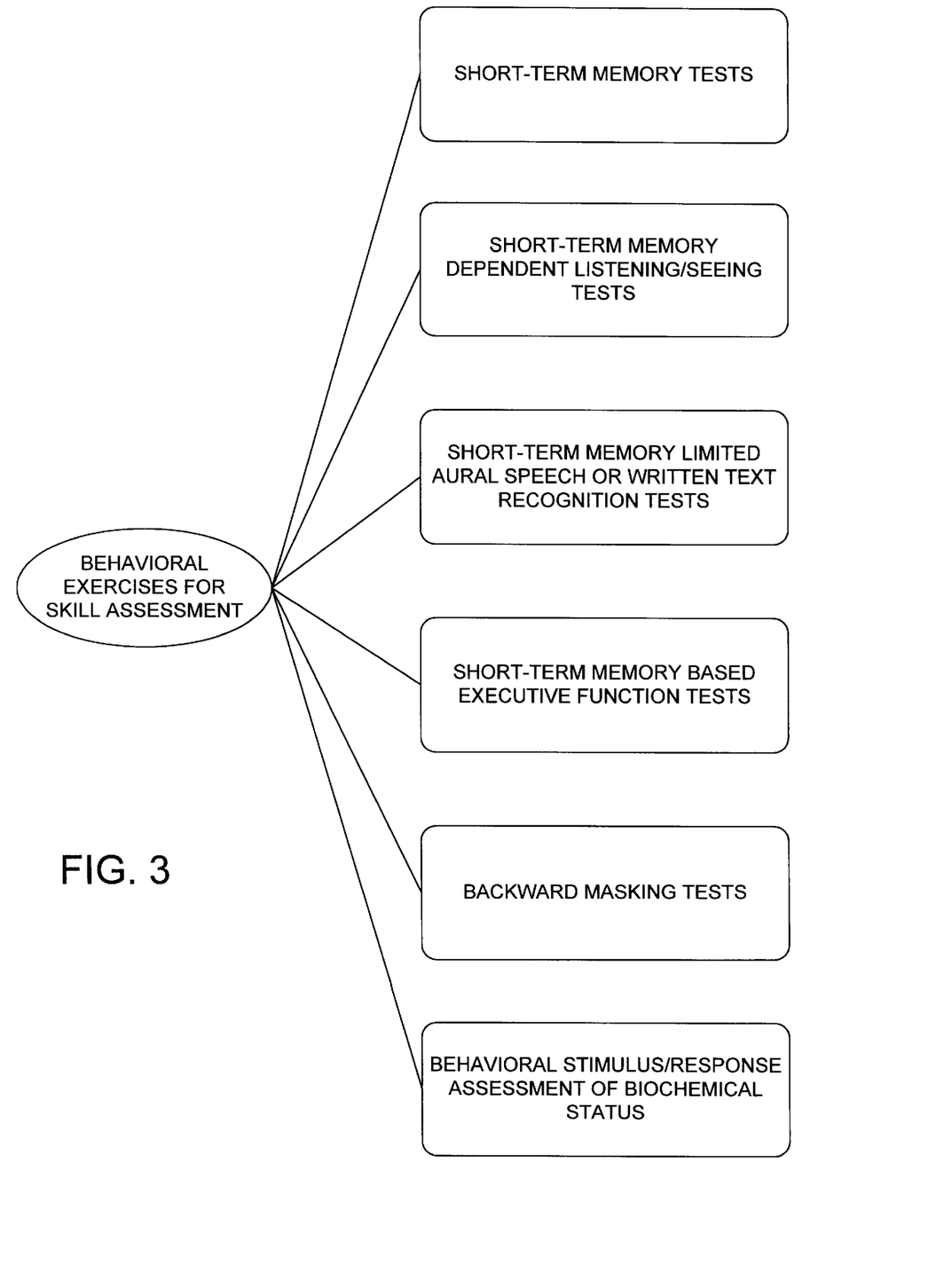
FIG. 3 illustrates some exemplary computer-implemented interactive behavioral training exercises that may be administered to a subject for schizophrenia risk assessment.

FIG. 3 illustrates some exemplary computer-implemented interactive behavioral training exercises that may be administered to a subject for schizophrenia risk assessment (step 202 of FIG. 2). It should be noted that the number and types of interactive behavioral exercises illustrated in FIG. 3 are only exemplary. Given the general principles discussed, other specific interactive behavioral exercises may be created for testing one or more of the skills discussed below.

By way of example, the subject may be tested for proficiency in short-term memory skills. The computer may present a subject with a list of items (e.g., words, numbers, objects) either aurally, pictorially, or in written form. The subject may then be asked to memorize the list and perform short-term memory type tasks such as repeating the list of items in the order of presentation, in reverse order, or in any order, distinguish the items presented from non-presented item(s), recall whether an item was presented, or the like.

Proficiency in short-term memory-dependent listening (or seeing) "vigilance" tasks may also be tested. By way of example, the computer may present the subject with a target item (e.g., word, picture, or sound). The subject may be asked to give a specific response each time the target item is again presented, or to count or match the target item with another item, or in another exercise epoch, to signal each time the target item is omitted.

Proficiency in short-term memory-limited aural speech or written text recognition tasks may also be tested. By way of example, the subject may be asked to perform according to simple verbal or written instructions from the computer, which instructions are hierarchical in their lengths and complexities. As another example, the computer may ask the subject to listen to (or read) a story and then to answer simple queries about its content.

Another test assesses the subject's ability to perform short-term memory-based executive functions. By way of example, the computer may ask the subject to solve simple logical puzzles. One such puzzle may be, for example, "if A is true, B is true; and if C is true, B is not true. Now decide which of the following statements is true." As another example, the subject may be asked to decide and make value judgments regarding a story told by the computer. Examples of queries given are: Who told the story? Who did they tell it to? Who received the prize? Who was punished unfairly, etc.

Backward masking may also be tested. In a backward masking task, the target visual, acoustic or speech signal precedes a rapidly following signal. The subject may be asked to signal when the initial signal is present, or may be asked to identify it. The abilities are assayed as a function of the strengths of the target signal and the following masker, as a function of their durations, and as a function of the time separation between them.

Assessment tests designed to more directly assay the subject's biochemical balance or imbalance may also be given. By way of example, visual contrast sensitivity measures may be employed to assess the level of retinal dopamine, which generally parallels dopamine expression contributing to certain schizophrenia symptoms. By measuring one's visual contrast sensitivity, the general dopamine expression status may be indexed, and employed to assess risk.

Figure 4:
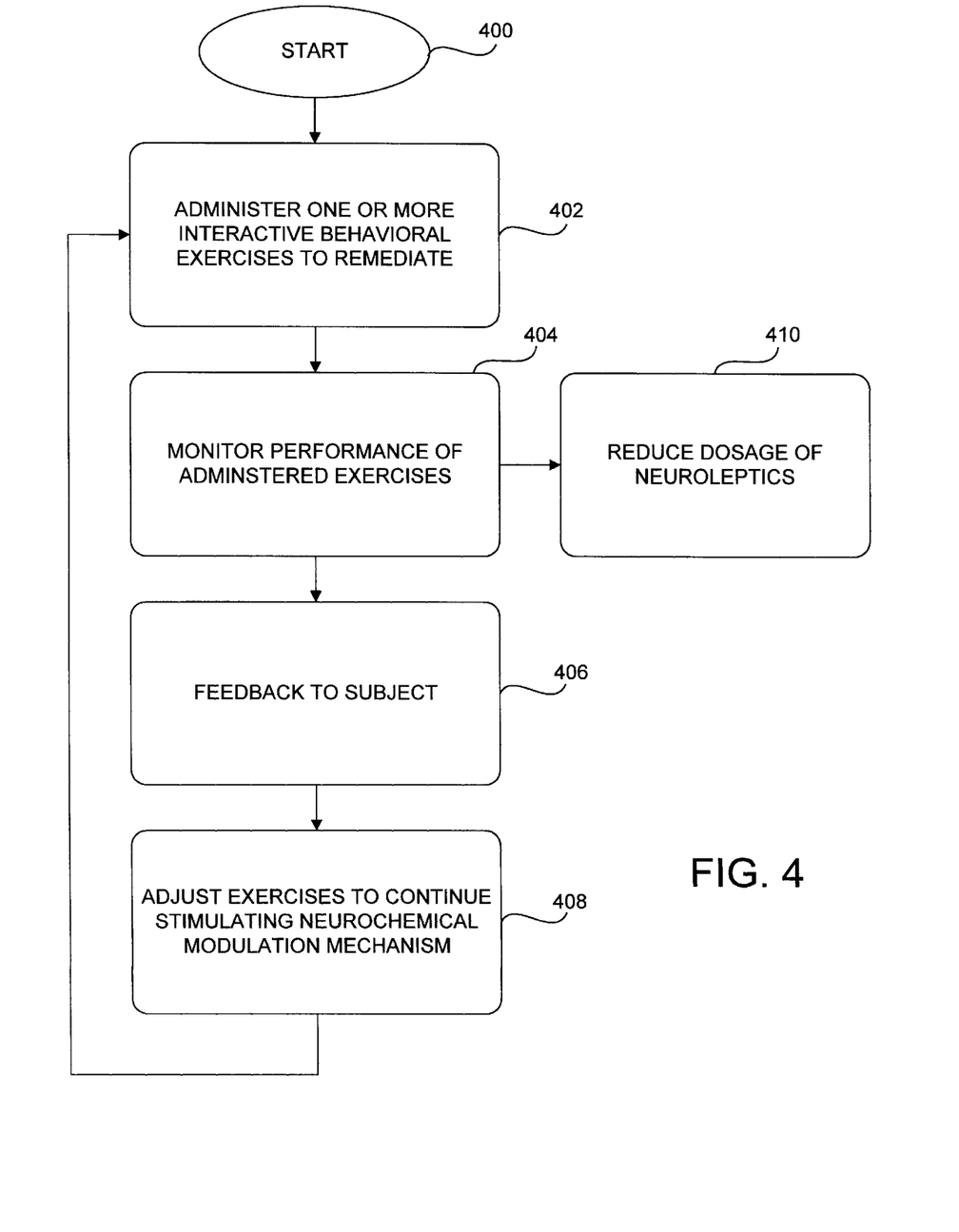
FIG. 4 illustrates, in accordance with one embodiment of the present invention, the steps involved in using interactive behavioral training to remediate schizophrenia.

FIG. 4 illustrates, in accordance with one embodiment of the present invention, the steps involved in using interactive behavioral training to remediate schizophrenia (e.g., step 206 of FIG. 2), either after the onset of clinically observable schizophrenia symptoms or before (i.e., for prophylactic purposes). The interactive behavioral exercises are administered in step 402 to the subject.

In step 404, the subject's performance in the interactive training exercises are monitored for improvement. The subject's trial-by-trial and overall progress for each session or each day may be recorded by the computer and provided to a supervising health care professional (e.g., a supervising psychiatrist or therapist), who may be informed on the same computer or at a remote computer through the computer network (e.g., a LAN, WAN, or the Internet). In this manner, the health care professional may be able to work with multiple subjects at once and may not need to be physically present. By monitoring the subject's progress, the health care professional may be informed about subject compliance and can intervene if the subject is not complying (which is common for schizophrenics as they tend to be in denial about their illness), is not working at the training exercises in the appropriate manner or is stalled (and therefore may require special assistance or switching to a different set of exercises).

Note that this monitoring may be performed throughout the exercises to continuously vary the level of difficulty to maintain a high level of attentional focus to facilitate expressions of neurochemicals and/or vary the number of trials to ensure that the neurotransmitter modulation mechanism is sufficiently stimulated. The adjustment of the training exercises is shown in FIG. 4 in step 408.

In step 406, feedback is preferably given to the subject pertaining to the subject's performance. As mentioned, the interactive training exercises are preferably chosen so that the subject is correct and rewarded a substantial percent of the trials attempted (with some relevant rewards, which may be intangible such as an audible or a visual presentation signaling a correct response, or a game, or more tangible rewards such as points or tokens that may be redeemable for cash, prizes, etc.). As mentioned, the rewards are intended to encourage and magnify normal controlled neurochemical release and to continue to motivate the subject to maintain sharply focused attention and vigilance, all of which affect the neurochemical imbalance in the subject's brain. In this respect, the present technique is different from the prior art since the frequency and emphasis on rewards are heightened to achieve a different result than merely improving each skill piecemeal.

Optionally, the present inventive training technique may be employed as an adjunct to conventional pharmacological approaches to treating schizophrenia. That is, the improvement provided by the interactive training may reduce or eliminate the dosage of neuroleptic drugs required for treating schizophrenia (step 410). The reduction may be performed according to dynamic tailoring techniques. Dynamic tailoring of dosages is discussed in detail in a commonly owned, co-pending patent application entitled "Methods And Apparatus For Dynamically Tailoring Biochemical Based Therapy Programs In Human", filed by inventors Steven L. Miller, Michael M. Merzenich, and Bret E. Peterson on Jun. 18, 1998 (application Ser. No. 09/100,663) which is incorporated by reference herein. Thus, the subject's schizophrenic symptoms may be brought under control more quickly through a combination of neuroleptic drugs and interactive training, with the dosages of the neuroleptic drugs steadily decreasing over time as the monitored performance improves.

As mentioned earlier, the interactive behavioral exercises are designed such that there is an intensive trial-by-trial attentional focus while at the same time ensuring that the patients are substantially rewarded for correct performances a substantial percent of the time (e.g., about 80% or more in one embodiment). Accordingly, the exercises are preferably adjusted automatically by the computer in step 408, responsive to the monitoring of step 404, to keep the tasks challenging. In one example, the subjects operate on a on a 3-up, 1-down staircase or other learning progression designed to assure that they get the substantial majority of trials "correct", e.g., when they get three "answers" correct in a row, the task becomes more difficult by one small difficulty step; while when they get one "answer" incorrect, the task becomes easier, by one difficulty step. Subjects may be rewarded not only when they get each correct answer, but also when they reach a particular task benchmark difficulty level. Subjects may work for pre-defined performance goals, and may rewarded when they reach goals and subgoals. Further, the subjects may be rewarded as a function of effort and the intensity of their attentional focus on the exercises. At the end of each training session, they may be informed about their progress toward reaching those goals. As mentioned, the emphasis on rewards and positive feedback is designed to stimulate the release of neurotransmitters in the forebrain and far in excess of what is typically required in the prior art to simply upgrade performance in a specific skill.

Additionally, it is preferable that a high number of trials per day be administered. By way of example, hundreds or thousands of trials per day may be administered to the subject to ensure that the neurochemical modulation mechanism is sufficiently stimulated. It is contemplated that training may last at least one hour per day and may extend to as many hours as necessary, limited only by the subject's interest level, stamina, and attentional focus. In general, about 1 to 3 hours per day may be devoted to training.

The exact number of trials depend on many factors, including the length of each trial (e.g., a story will take longer to absorb than a set of stimuli consisting of two audible tones), the attentional focus required (which limits the mental endurance of the subject), and the like. These trials may relate to a single skill or to different skills to be trained during the training day. The training of all relevant skills may take place during a single day or on different days. It is preferable, although not absolutely necessary, that training be performed every day to ensure continued progress. Irrespective of the exact format, the intensive interactive behavioral exercises are configured to be sufficiently intensive in the number of trials to fundamentally change the expression of neurotransmitter in the brain to address the neurochemical imbalance believed to underlie schizophrenia. In this respect, the result sought and achieved is different in kind than that achieved by the prior art piecemeal training approach in which such intensiveness is either lacking or unnecessary to achieve improvement by rote in a specific skill. Some exemplary training exercises that may be employed to remedy schizophrenia are discussed later herein.

Within the general guidelines discussed herein, the exact interactive exercises that would work effectively could vary greatly. By way of example, the subject may be trained using paired associate learning exercises in which the subject may be asked to learn each aurally or orthographically presented word or each of a series of pictures as both a stimulus and a specific response (paired associate). In this exercise, they may be asked to correctly identify the aurally presented word with its orthographic (written) and pictorial forms; and may also be asked to correctly identify the "associate" in any one of these three forms, as requested. Difficulty in this exercise may be controlled by expanding the length of the list of paired associates; by separating the time of presentation of a target associate from the initially presented item; and by adding hierarchical levels to the associative task, e.g., first I might associate "cow" with "farm"; at a higher level I might have to associate it "farm" AND "barn" AND "pasture", or with all things on the farm; etc.

As another example, the subject may be trained using stimulus categorization/association exercises in which the subject works through extensive compendia of normally associated aurally presented words, written words and pictorial representations of objects, actions and relationships. Subjects work at categorization (sorting) of stimuli that belong together, i.e., that are normally associated. Difficulty level parallels the strength of that normal association. Again, this exercise may be heavily loaded with social skills and executive skills-related associations.

As a further example, the subject may be trained using story recall exercises in which the subject is asked questions about a story after hearing it. Task difficulty may be varied by increasing story length, complexity, question length, question complexity, and the time separation between story iteration and querying. At least two executive function skills may be incorporated into these exercises: decision making based on logic presented in the story; and identification of the sources in the story of particular actions or relationships. This task may also be heavily loaded with social skills training scenarios.

As a further example, the subject may be trained with short term memory span exercises in which the subject is presented with a list of aurally presented (written, picture) items; they are required to reiterate them in order; to reiterate them in reverse order; to reiterate them in a second mode; to reiterate them in anything except their serial order; etc. The main variables of the exercises may be the list lengths, task associations, task complexity.

As a further example, the subject may be trained using serial memory/trail-tracking exercises in which the subject may be asked to organize a set of symbols or numbers or letters in a required or in a logical sequence. For example, a subject may be asked to signal by a mouse press when they hear numbers in normal or backward sequence. They might hear "one" (press), "four" (don't press"), "two" (press), "one" (don't press), "three" (press), etc. Or, they may signal and reconstruct a sequence of numbers by pressing randomly distributed circles on which numbers are presented. Or they may signal a logical sequence by picking out and ordering pictures that represent all of the parts of a simple stated act ("Johnny drives to the grocery story to buy groceries for supper, which Sally prepares before Johnny goes out to the baseball game."). The main variables of the exercises may be list lengths, object/number sizes and randomization, number of presented foils, and task complexity.

As a further exercise, subjects may be asked to participate in continuous attention/vigilance exercises in which they receive a target word aurally (written, pictorially), and may be asked to mouse press every time they hear it (see it written, see it pictorially), or each time they hear (see) a written word (see a picture) that relates closely to it. Variables include the probability of target word presentation; the number of foils presented in the background; aural word to written word/pictorial word associations; and word association complexities.

As a further example, the subject may be trained with exercises aimed primarily at their social/executive skills training. By way of example, they can be presented with a social scene with actors and receivers of action with different facial expressions. They can be queried about appropriate and inappropriate actors or receivers of action, about sources of action in the scene, or about their own actions or behaviors in this social setting.

As a further example, the subject may be trained with exercises aimed primarily at their speech reception/language reception. It is noted that the majority of schizophrenics have speech/language reception deficits. In those subjects, four modified exercises in the Fast ForWord™ fundamental language listening skills training program shall be administered in schizophrenia training. Fast ForWord™ is a computer-implemented language skills program that may be obtained by contacting Scientific Learning Corporation of Berkeley, Calif. In these exercises, the spectrotemporal details of speech are disambiguated by lengthening and differentially strengthening the relatively fast, weak sound components in the acoustic speech input stream. Once subjects master tasks conducted with speech in this disambiguated form, they are then trained to distinguish speech in progressively higher-speed (less acoustically modified, more normal) forms. Task difficulty is primarily by adjusting the extent of acoustic signal modification over time, i.e., by progressively fading the processing, and by increasing the memory or discriminative perceptual or cognitive demands of each task.

While this invention has been described in terms of several preferred embodiments, there are alterations, permutations, and equivalents which fall within the scope of this invention. It is therefore intended that the following appended claims be interpreted as including all such alterations, permutations, and equivalents as fall within the true spirit and scope of the present invention.

What is claimed is:

1. A computer-implemented method for remediating schizophrenia in a person, comprising:
   (a) assessing, using a computer-implemented interactive behavioral assessment regime, a schizophrenia risk factor for said person;
   (b) if said schizophrenia risk factor is greater than a predefined benchmark, periodically reassessing said schizophrenia risk factor by
      waiting for at least a predefined period of time, and
      performing step (a) after said predefined period of time expires;
   (c) if said schizophrenia risk factor is below said predefined benchmark, treating said person by
      administering computer-implemented interactive behavioral training to said person, said computer-implemented interactive behavioral training being sufficiently intensive during each training day to drive a neurochemical change in said person's brain to remediate said schizophrenia over time.

2. The computer-implemented technique of claim 1 wherein said computer-implemented interactive behavioral training is configured to permit said human to be correct in at least 50% of the training administered.

3. The computer-implemented technique of claim 1 wherein said computer-implemented interactive behavioral training involves at least two of a set of tasks that includes perceptual, cognitive, executive, and social tasks, wherein said person is trained for at least 100 trials in each of said at least two tasks per training day.

4. The computer-implemented method of claim 1 further including providing, using said computer-implemented approach, feedback to said person.

5. The computer-implemented method of claim 4 further including rewarding, using said computer-implemented approach, said person.

6. The computer-implemented method of claim 1 wherein administering said computer-implemented interactive behavioral training includes administering a set of computer-implemented exercises.

7. The computer-implemented method of claim 6 wherein said set of computer-implemented exercises includes one of an auditory test, a visual test, a behavioral test and a cross-stimulus test.

8. The computer-implemented method of claim 6 further including altering said set of computer-implemented exercises.

9. The computer-implemented method of claim 6 wherein altering said set of computer-implemented exercises is directed such that said person can correctly respond to approximately 80% of said set of computer-implemented exercises.

10. The computer-implemented method of claim 6 wherein administering said computer-implemented interactive behavioral training includes a number of exercises effective to reduce the effects of schizophrenia within said person.

11. The computer-implemented method of claim 10 wherein said number of exercises includes one hundred tests in a single day.

12. The computer-implemented method of claim 1 wherein said computer-implemented interactive behavioral training is directed to improve a skill for said person.

13. The computer-implemented method of claim 12 wherein said skill is one of a perceptual skill, a cognitive skill, a social skill and an executive function skill.

14. The computer-implemented method of claim 12 wherein said skill is not identified as deficient in said person.

15. The computer-implemented method of claim 1 wherein said computer-implemented interactive behavioral training is directed to promote inter-related skills.

16. The computer-implemented method of claim 1 wherein administering said training regime is performed a number of times effective to reduce the effects of schizophrenia within said person.

17. The computer-implemented method of claim 16 wherein administering said training regime is performed on a daily basis.

18. The computer-implemented method of claim 1 wherein administering said training regime is performed prophylactically.

19. The computer-implemented method of claim 1 wherein said computer-implemented interactive behavioral training is directed to elicit a high level of engagement from said person.

20. The computer-implemented method of claim 1 further including providing, using said computer-implemented approach, said schizophrenia risk factor to a health care professional.

21. The computer-implemented method of claim 1 wherein said training regime is employed as an adjunct to a pharmaceutical approach.

22. A computer readable medium for remediating schizophrenia for a person, said computer readable medium comprising:

(a) instructions for assessing, using a computer-implemented interactive behavioral assessment regime, a schizophrenia risk factor for said person;

(b) instructions for, if said schizophrenia risk factor is greater than a predefined benchmark, periodically reassessing said schizophrenia risk factor by
waiting for at least a predefined period of time, and
performing (a) after said predefined period of time expires;

(c) instructions for, if said schizophrenia risk factor is below said predefined benchmark, treating said person by
administering computer-implemented interactive behavioral training to said person, said computer-implemented interactive behavioral training being sufficiently intensive during each training day to drive a neurochemical change in said person's brain to remediate said schizophrenia over time.

23. A computer implemented method for delivering computer readable instructions for remotely remediating schizophrenia for a person, said method being implemented using a computer network having a monitoring computer and a remote administering computer, said remote administering computer being geographically remote from said monitoring computer and local to said person, said method comprising:

(a) transmitting, over a signal transmission medium, signals representative of instructions for assessing, using a computer-implemented interactive behavioral assessment regime, a schizophrenia risk factor for said person;

(b) transmitting, over a signal transmission medium, signals representative of instructions for, if said schizophrenia risk factor is greater than a predefined benchmark, periodically reassessing said schizophrenia risk factor by
waiting for at least a predefined period of time, and
performing (a) after said predefined period of time expires;

(c) transmitting, over a signal transmission medium, signals representative of instructions for, if said schizophrenia risk factor is below said predefined benchmark, treating said person by
administering computer-implemented interactive behavioral training to said person, said computer-implemented interactive behavioral training being sufficiently intensive during each training day to drive a neurochemical change in said person's brain to remediate said schizophrenia over time.

* * * * *